United States Patent
Clark et al.

(10) Patent No.: US 6,879,421 B2
(45) Date of Patent: Apr. 12, 2005

(54) METHOD AND SYSTEM FOR PERFORMING SWEPT-WAVELENGTH MEASUREMENTS WITHIN AN OPTICAL SYSTEM INCORPORATING A REFERENCE RESONATOR

(75) Inventors: Bryan Clark, Mountain View, CA (US); Andrei Brunfeld, Cupertino, CA (US)

(73) Assignee: Beyond 3, Inc., Fremont, CA (US)

( * ) Notice: Subject to any disclaimer, the term of this patent is extended or adjusted under 35 U.S.C. 154(b) by 0 days.

(21) Appl. No.: 10/750,747

(22) Filed: Jan. 2, 2004

(65) Prior Publication Data

US 2004/0190148 A1 Sep. 30, 2004

Related U.S. Application Data

(63) Continuation-in-part of application No. 10/403,238, filed on Mar. 28, 2003, now Pat. No. 6,778,309.

(51) Int. Cl.[7] .......................... G02F 1/00; G01N 21/00; H01S 3/10
(52) U.S. Cl. ................. 359/237; 359/245; 359/260; 356/237.2; 356/450; 356/519; 356/5.05; 372/20
(58) Field of Search ............................... 359/237, 245, 359/260, 318; 356/237.2, 450, 519, 5.05, 479, 502; 372/20, 32

(56) References Cited

U.S. PATENT DOCUMENTS

| | | | | |
|---|---|---|---|---|
| 4,738,527 A | * | 4/1988 | McBrien | 356/5.05 |
| 4,830,486 A | | 5/1989 | Goodwin | 356/4.06 |
| 5,345,328 A | * | 9/1994 | Fritz et al. | 359/248 |
| 6,594,022 B1 | * | 7/2003 | Watterson et al. | 356/519 |

* cited by examiner

Primary Examiner—Timothy Thompson
Assistant Examiner—M. Hasan
(74) Attorney, Agent, or Firm—Andrew M. Harris; Harry M. Weiss; Weiss, Moy & Harris, P.C.

(57) ABSTRACT

A method and system for performing swept-wavelength measurements within an optical system incorporating a reference resonator provides improved operation in resonator-enhanced optical measurement and data storage and retrieval systems. The system includes an illumination subsystem, an illumination coupler for producing a measurement beam and a reference beam from an output of the optical illumination source, a reference resonator for receiving the reference beam, a measurement resonator for receiving the measurement beam, at least two detectors, one optically coupled to the reference resonator and one optically coupled to the measurement resonator, and a time-domain measurement system coupled to the detectors for comparing detected optical signals received from the resonators. The detected signal from the reference resonator is used to compensate or detect variations in the wavelength of the illumination system, improving the resolution and accuracy of the measurement provided by the measurement resonator.

22 Claims, 4 Drawing Sheets

METHOD AND SYSTEM FOR PERFORMING SWEPT-WAVELENGTH MEASUREMENTS WITHIN AN OPTICAL SYSTEM INCORPORATING A REFERENCE RESONATOR

RELATED APPLICATIONS

This application is a continuation-in part of U.S. Patent Application "METHOD AND SYSTEM FOR PERFORMING SWEPT-WAVELENGTH MEASUREMENTS WITHIN AN OPTICAL SYSTEM", Ser. No. 10/403,238, filed on Mar. 28, 2003 now U.S. Pat. No. 6,778,309, the specification of which is incorporated herein by reference.

BACKGROUND OF THE INVENTION

1. Field of the Invention

This invention relates to optical systems, and more specifically, to a swept wavelength optical system that incorporates a coherent interference in both a reference path and a measurement path.

2. Description of the Related Art

Optical measurement systems, optical storage and retrieval systems and other optical systems may be limited by many factors, including illumination beam size, diffraction limit, detector noise, and resolution. The above-incorporated patent application discloses swept-wavelength techniques for enhancing the performance of a variety of optical systems and improving the resolution and sensitivity of optical technologies disclosed therein. It would be further desirable to improve the performance of the systems disclosed in the above-referenced patent application, as well as other optical systems, in order to further improve their performance.

The system phase accuracy requirement in some measurement applications requires the wavelength control to meet or exceed 0.01% of the wavelength. Further, the resonator further multiplies deviations in phase by the cavity length. With a resonator length of 10000λ, phase control to 0.01% of the wavelength dictates control of the illumination wavelength to within 1 part in a hundred million or better, which is difficult or impossible to stably achieve while maintaining high speed operation by using a tunable illumination source and feedback loop. The above-incorporated patent application overcomes this barrier by providing a swept-wavelength system and method, that do not require a phase-stable source. However, variations in wavelength in terms of wavelength offset, drift and jitter are difficult to manage in a swept-wavelength measurement system. In particular, sufficiently agile sources are even more difficult to stabilize than fixed-wavelength sources due to the rapidly tunable nature of the source, as any cavity used to stabilize or otherwise operate the laser must be tuned in the wavelength sweeping process or must be sufficiently broadband that stabilization is essentially not provided by the cavity. Further, in an electrically swept illumination subsystem such as those employing an electrically-tunable laser diode, electrical noise in the control system or at the junction itself provides phase variation or jitter.

Therefore, it would be desirable to provide an alternative method and system for swept-wavelength measurement that overcomes the stability limitations of the illumination source.

SUMMARY OF THE INVENTION

The foregoing objectives are achieved in an optical system and method and apparatus for optical measurement. The system includes a swept-wavelength optical illumination subsystem, an illumination coupler for producing a measurement beam and a reference beam from an output of the optical illumination source, a reference resonator for receiving the reference beam, a measurement resonator for receiving the measurement beam, at least two detectors, one optically coupled to the reference resonator and one optically coupled to the measurement resonator and a time-domain measurement system coupled to the detectors for comparing detected optical signals received from the detectors, so that the reference resonator measurement is used to compensate for variations in the wavelength of the illumination subsystem.

In particular, components of the time-domain analysis provide information about changes in the wavelength of the measurement by using the reference resonator swept-wavelength response in comparison to the measurement resonator response. The measured changes permit determination of variations in the measurement wavelength and/or variations in the measurement resonator, and can be used to provide feedback for adjusting the illumination wavelength or effective cavity length of the measurement resonator.

The foregoing and other objects, features, and advantages of the invention will be apparent from the following, more particular, description of the preferred embodiment of the invention, as illustrated in the accompanying drawings.

DESCRIPTION OF EMBODIMENTS OF THE INVENTION

Figure 1:
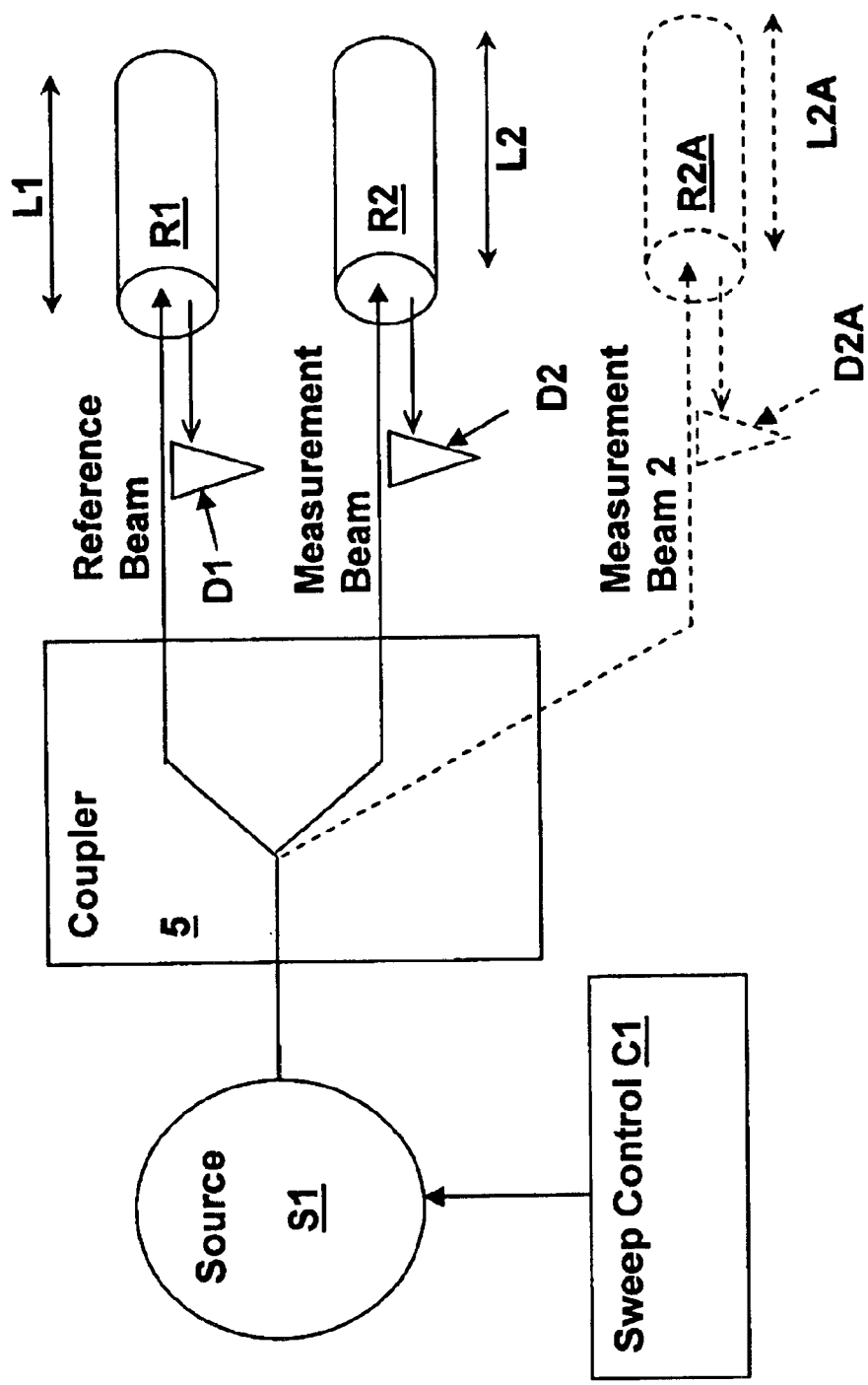
FIG. 1 is an illustration depicting an optical system in accordance with an embodiment of the present invention.

The above-incorporated parent application describes a swept-wavelength technique and system that can be used to improve the performance of various resonator-enhanced optical systems. However, the accuracy of the techniques disclosed in the above-incorporated parent application is limited by a number of factors, the primary limitation being uncertainty in the wavelength of the illumination source due to factors such as coherence and emission linewidth, changes in the active media refractive index and/or the laser's optical length. Metrologically, the illumination wavelength is the measurement etalon and due to the large number of wavelengths in a typical measurement path, a small change in wavelength has a large effect on the measured results. Therefore, the illumination source in an optical measurement system must typically be stabilized to a level of $10^{-8}$ wavelength or in some cases down to $10^{-9}$ wavelength through known techniques of cavity and/or laser control.

Tunable sources, such as those employed to provide swept-wavelength measurements are especially prone to variations and/or deviation from expected wavelength profiles, as the required agility of the source and the rate at which the wavelength must be swept in essence determine a maximum "Q" of the associated cavities. The resonators used within tunable lasers have relatively lower Qs than fixed frequency sources and the amount of wavelength jitter is consequently higher, causing an enlarged linewidth (decreased temporal coherence). Further, the electrically tunable lasers employed in swept-frequency measurements are sensitive to noise, offset and drift in the control voltage, which tends to increase the amount of jitter and also adds an uncertainty in the illumination wavelength due to offset and drift. Electrically tunable resonators, if such are employed, are subject to the same variations, although non-tuneable resonators are still prone to quantum and environmental changes that affect the optical path length of the resonator.

The present invention provides a significant accuracy improvement to the techniques disclosed in the above-incorporated parent application that reduce the impact of uncertainty in the optical illumination source wavelength and/or the optical path length of the resonator. A second resonator is employed so that differential analysis of the measured return intensities of the resonator may be used to remove the above-mentioned uncertainties from a measurement. As mentioned above with respect to the illumination wavelength as the measurement etalon, in the present invention, the reference is changed from the wavelength to an optical path length of a passive etalon. The passive etalon incorporated in the system of the present invention is a resonator having a very stable or predictable optical path length. The passive etalon can be of the same order or identical to the measuring etalon, yielding a greatly reduced relative error.

The measurement techniques use a time domain detection analysis that are applied to both a reference resonator and a measurement resonator. The present invention uses time domain analysis to determine changes in the effective length of the measurement resonator as related to the reference resonator length (rather than to the illumination wavelength), thereby correcting for uncertainty in the illumination wavelength or other system variation by a time domain analysis of the reference resonator response. The present invention may also correct other measurements cavity changes mentioned in the above-incorporated parent application, such as when a surface of the measurement resonator is a surface under measurement with features detected by the time domain analysis, such as reflectivity/absorption, polarization, scattering (e.g. surface roughness), and so forth.

A swept wavelength illumination source is used to vary the effective length of both the reference resonator and the measurement resonator through several discrete resonance points. The time domain relationship of each resonator's resonance points contains information about the cavity length, as the spread of the resonance points (detectable as pulses or other variations in the time domain detected signal) varies with wavelength. Thus, both instantaneous changes in the detected signal time domain profile and the time domain profile it self can be analyzed to determine cavity length, cavity length changes or both. The time domain profile can be examined (or initially detected) to find any combination of pulse position, pulse width, pulse height and pulse shape. The information from the time domain analysis can be used to determine cavity length, resonance "Q" (which may indicate a gross variation in cavity length or a change in reflectivity/absorption/scattering, etc.)

With reference now to the figures, and in particular to FIG. 1, an optical system in accordance with an embodiment of the invention is depicted. An optical illumination source S1 is swept in wavelength under the control of sweep control C1. Illumination source will generally be a laser diode having a tunable cavity, but other sweepable illumination sources may be used such as broadband lasers having tuneable optical filters for sweeping the filter passband to yield a swept-wavelength illumination subsystem. A coupler 5 divides the output of illumination source S1 into a reference beam and a measurement beam. The measurement beam is introduced to a measurement resonator R2 and the reference beam is introduced to a reference resonator R1. Measurement resonator R2 is inserted in a measurement path of the optical system, and part of the resonant structure may be a surface under measurement, so that the response of resonator R2 as measured by a return intensity as detected by a detector D2 is indicative of a characteristic of the surface under measurement (e.g., surface height or reflectivity). Also, a transmitted intensity through resonator may alternatively be measured by detector D2 (if detector D2 is positioned to measure the intensity of a beam transmitted through resonator R2) or another detector may be used in concert with detector D2 to measure both transmitted and reflected intensity from resonator R2.

While the response at detector D2 may provide an indication of the measured characteristics of a surface, uncertainty in the wavelength of illumination source S1, or other variations in path length of the measurement path will yield error (deviations) in the response at detector D2 from the desired or expected response. Reference resonator R1 provides correction for the above-mentioned deviations by providing a stable reference response at detector D1 from which the wavelength of illumination source S1 can be established at particular points in time. By processing the outputs of detectors D1 and D2 in a differential measurement that compensates for the above-mentioned variations, the resolution of the optical system is greatly enhanced.

Coupler 5 can have a ratio determined by the particular application. In general, only a small portion of the intensity of source S1 need be coupled to reference resonator R1, as reference resonator can be designed so that a high level of reflectivity is produced at maxima of the resonance waveform generated by the swept wavelength illumination. Measurement resonator R2 may therefore advantageously use the higher illumination intensity coupled from coupler 5 in order to measure, for example, a surface having a high degree of dispersion or a low reflectivity. Reference resonator R1 can be a very stable resonator, as no moving parts or tunability is required for the reference resonator R1. Either resonator may be a Fabry-Perot resonator, or one may be Fabry-Perot and the other another form of resonator. As reference resonator R1 does not require tuning or scanning, it may be made from temperature stable materials in a solid housing and the size of resonator R1 may not be a critical factor, permitting mounting of reference resonator R1 outside of a scanning head that includes measurement resonator R2.

Additional reference resonators (R2A coupled to detectors D2A and having path lengths L2A) may be added to the system to provide further improvement in reduction of measurement uncertainty. In general, it may be desirable to have reference resonators of differing but similar lengths in the system, since the path length measurement sensitivity varies with the illumination wavelength. For example, a number of reference resonators R2A may be employed, each having a resonance peak equally distributed within a half-wavelength of the expected illumination wavelength, so that at least one of the resonators will be operating near a region of highest sensitivity in the resonator response. Alternatively, or in concert, similar resonators may be used to determine variations in characteristics of the reference resonators themselves (e.g., variations due to temperature, imposed electromagnetic fields that affect the refractive index, mechanical strain and so forth).

The propagation length in the system must be taken into account, i.e., the differences between the reference optical path and the measurement optical path from the point of splitting in coupler 5, so that phase differences between the measurement beam and reference beam do not introduce significant de-correlation of the wavelength variations and degrade the accuracy of the measurements. A propagation path difference of 298 mm introduces a time/phase shift of 1 nanosecond and introduces a noticeable de-correlation of the wavelength variations. Optical path matching techniques are well-known in the art, so are not discussed herein.

Figure 2:
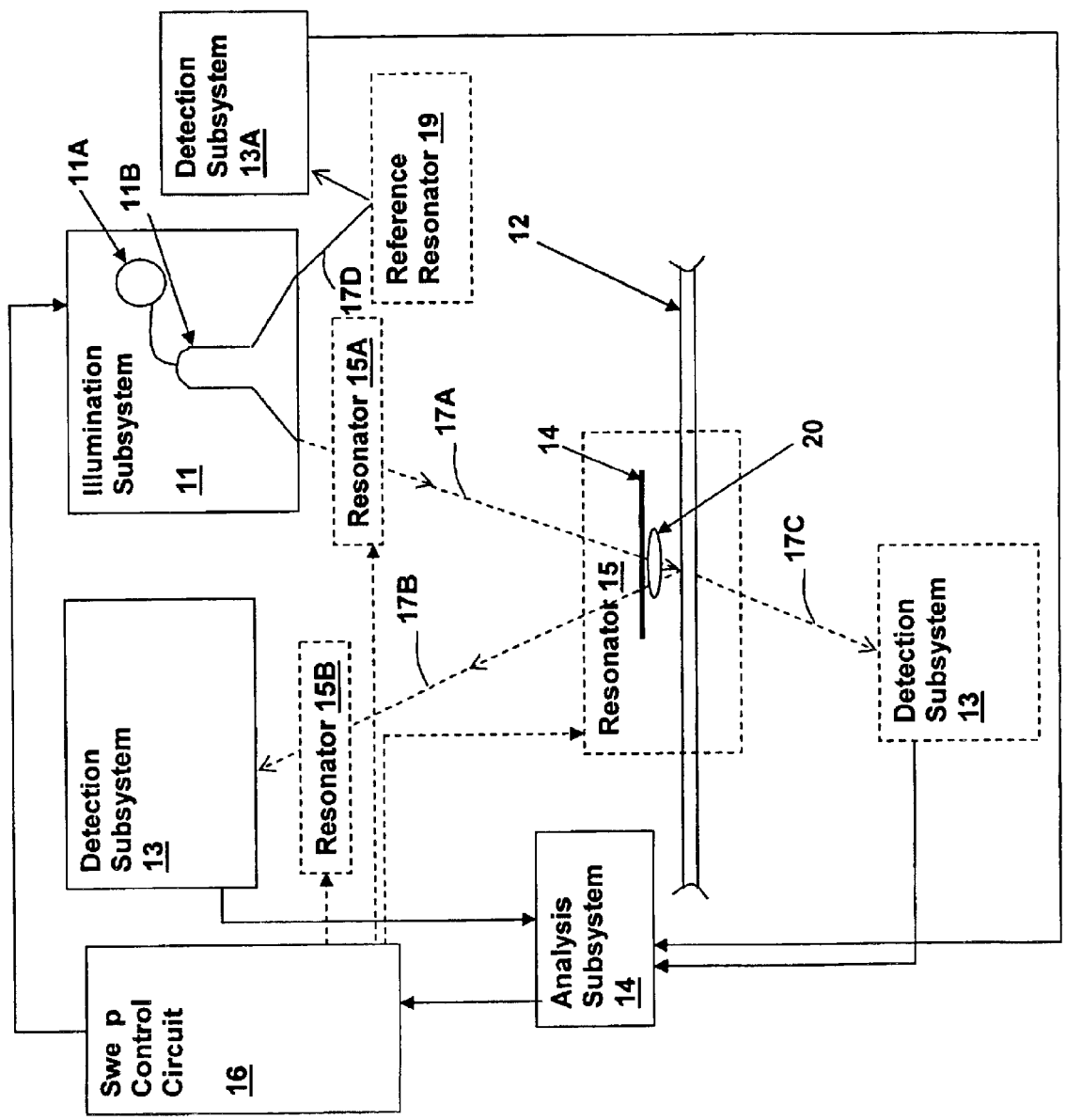
FIG. 2 is an illustration depicting another optical system in accordance with an embodiment of the present invention.

With reference now to FIG. 2, a surface or volume 12 including features under detection or data that is being extracted is illuminated by a tunable illumination subsystem 11 that produces an illumination beam 17A and a reference beam 17D. Illumination source 11A is introduced to splitter 11B which divides the illumination source output into measurement illumination beam 17A and reference beam 17D. A reflected beam 17B and/or a transmitted beam 17C is detected by a detection subsystem 13 (shown at two alternative positions), providing measurement information or data extraction. A measurement resonator 15, 15A or 15B is positioned within the optical path of the illumination beam 17A, reflected beam 17B and/or transmitted beam 17C. Illumination subsystem 11 has at least a swept-wavelength operating mode responsive to sweep control circuit 16, which sweeps illumination subsystem 11 through multiple resonant points of resonator 15, 15A or 15B. An analysis subsystem 14 determines a time-domain relationship between the resonances encountered by sweeping the illumination wavelength, and cavity length or changes in cavity length or finesse of resonator 15, 15A or 15B are thereby determined. The cavity length, finesse or changes therein may be used directly as a measurement output where the cavity length provides the desired measurement information. For example, in measurement systems where the features of surface or volume under measurement 12 cause variation in the cavity length of resonator 15, the information extracted by analysis subsystem 14 contains the feature information.

Reference beam 17D is introduced to reference resonator 19 and the resulting intensity is detected by a second detection subsystem 13A that is further coupled to analysis subsystem 14. (Detection subsystem 13A is shown as a reflection detector, but alternatively detection subsystem 13A may be coupled to measure transmission through reference resonator 19.) The intensity measured by detection subsystem 13A is used to correct or evaluate the intensity detected by detection subsystem 13 at each moment in time, so that variations of the wavelength of illumination source 11A and/or variations in the path length of the measurement beam (including variations within resonators 15 15A and 15B that are not due to the measurement function) can be reduced or eliminated in the measurement output.

In an alternative closed-loop feedback control system embodiment, the optical system may subsequently be tuned at a predetermined operating point in a constant-wavelength mode of illumination subsystem 11. The operating wavelength may be determined in conformity with the response detected from reference resonator 19 or from both reference resonator 19 and measurement resonator 15, 15A or 15B to provide the desired characteristics at detection subsystem 13.

In beam narrowing applications, resonator 15A is employed to reduce the profile of illumination beam 17A.

Resonator 15A may be included within illumination subsystem 11 or located between illumination subsystem and surface 12 as shown. Alternatively, or in combination, resonator 15 may be employed at surface 12 to increase sensitivity of the optical system. Resonator 15 includes a partially reflective surface 14 positioned above surface 12 at a predetermined distance to provide a predetermined resonance operating point, and may include a lens 20 that maps a region of partially reflective surface 14 to a region of surface of interest 12 improving the resolution of resonator 15. A similar resonant structure may be employed within reference resonator 19, including a lens, or reference resonator 19 may be any other resonant structure as is known in the art.

Detection subsystems 13 and 13A provide information to analysis subsystem 14 so that the time domain relationship of resonance points can be determined, which is generally a pulse-shaped variation in intensity level (which may be "dark" or "gray" level) of an interferometric fringe detector. Analysis subsystem 14 extracts information relating to one or more of the pulse peak positions (and differences between pulse peak positions), pulse width, pulse height and pulse shape.

Tuning of resonator 15, 15A or 15B may or may not be implemented in systems in accordance with various embodiments of the present invention. Since the measurement system is capable of determining multiple resonance points and their time relationships when illumination subsystem 11 is in swept-wavelength mode, it may not be necessary or desirable to provide other than a generally fixed cavity length for resonator 15, 15A or 15B (ignoring the actual cavity length variations provided by surface under measurement 12) and a well-established cavity length for reference resonator 19. However, when it is desirable to tune resonator 15, 15A or 15B, tuning may be accomplished by various means as described in the above-incorporated parent application.

Tuning (including sweeping) of illumination source 11 may be accomplished by use of a broadband laser/tunable filter such as the external cavity laser (ECL) or semiconductor tunable lasers such as Distributed-feedback (DFB) lasers, distributed Bragg reflector (DBR) lasers and vertical cavity surface emitting lasers (VCSEL).

Figure 3:
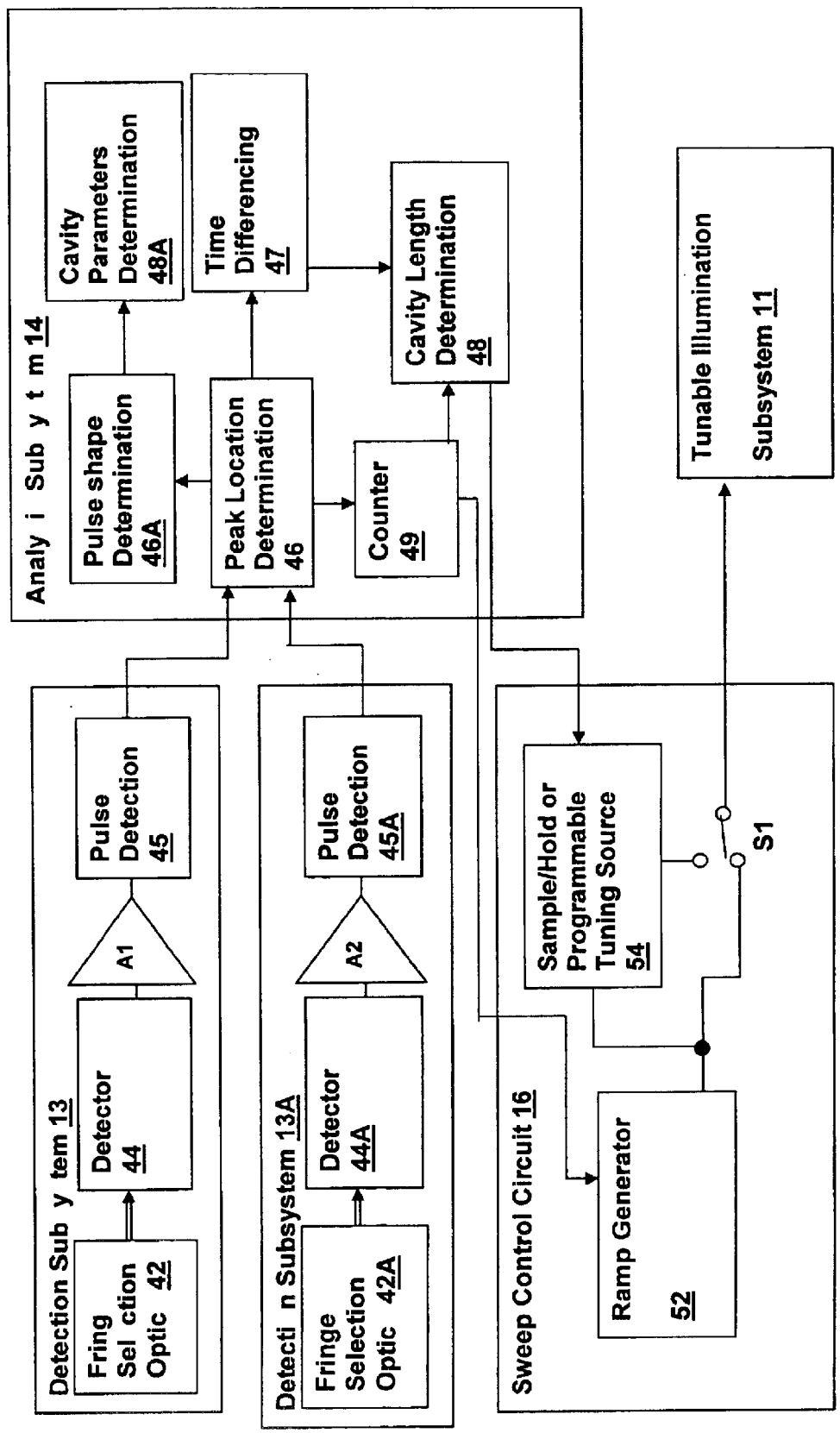
FIG. 3 is a block diagram showing details within the optical system of FIG. 2.
Figure 4:
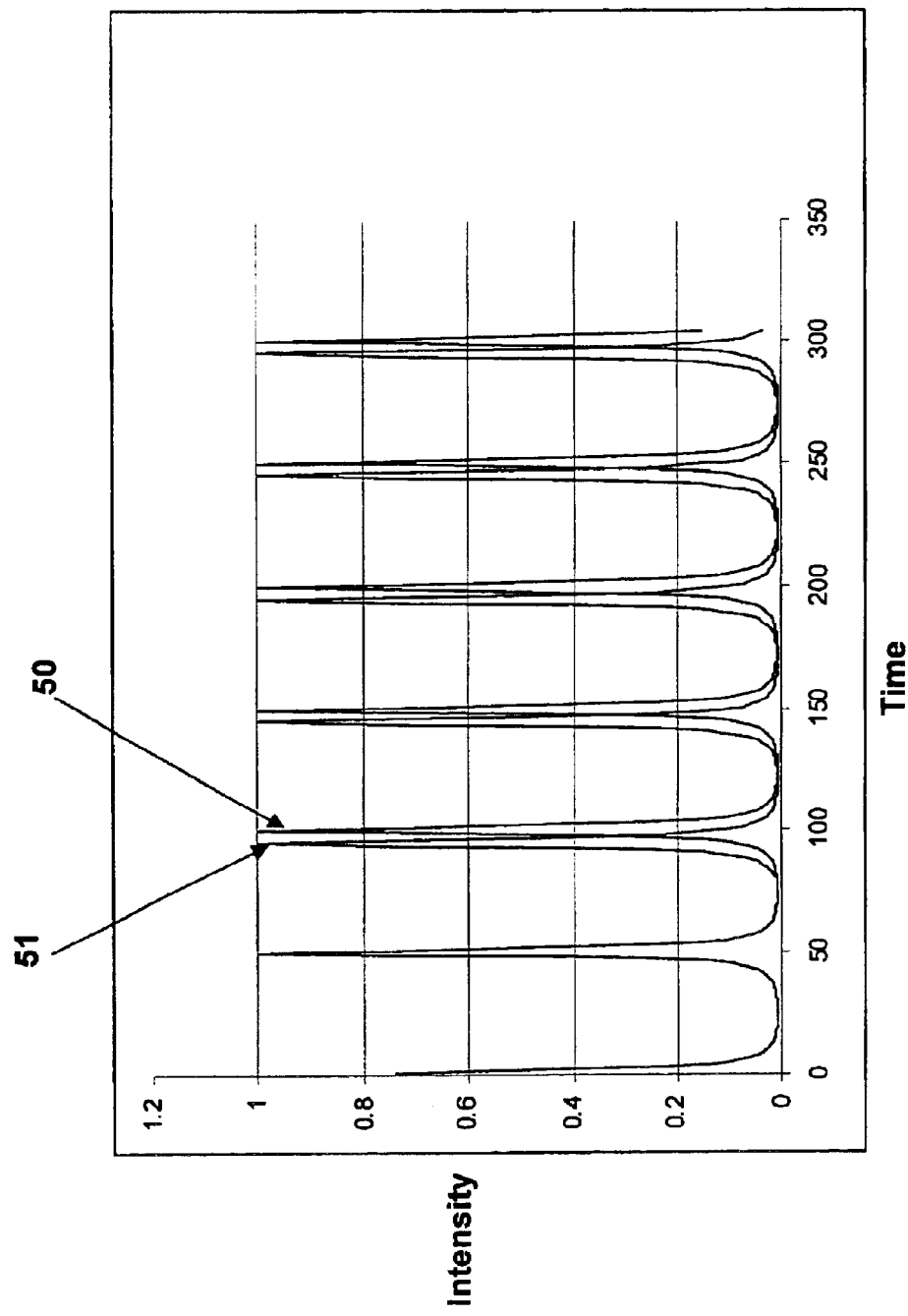
FIG. 4 is a graph depicting detected intensity measurements in an optical system in accordance with an embodiment of the present invention.

Referring now to FIG. 3, details of th e detection and control systems in accordance with embodiments of the present invention are depicted. Detection subsystems 13 and 13A include fringe selection optics 42 and 42A that select the interferometric detection point as the output to detectors 44 and 44A. Amplifiers Al and A2 adjust the gain and offset of detector 44 and 44A outputs to provide a control signal to pulse detection circuits 45 and 45A. Pulse detection circuits 45 and 45A are designed to match the shape of the pulses received by detection subsystems 13 and 13A, which will generally follow the shape of the Airy-function (for a linearly changing illumination wavelength) that describes the characteristic response of the resonator as shown in FIG. 4. Pulse detection circuits 45 and 45A may employ matched filters or other correlation blocks, in order to maximize the received signal-to-noise ratio in conformity with a predictable pulse shape.

The outputs of detection subsystems 13 and 13A enter peak location determination block 46 within analysis subsystem 14. Peak location determination block 46 determines a time relationship of multiple resonance peaks occurring in measurement resonator 15, 15A or 15B and reference resonator 19 as the wavelength of illumination subsystem 11 is swept in swept-wavelength mode. Peak location determination block may be a threshold comparator, but preferably a partial response detector or other precision pulse position estimation circuit having a characteristic suitably matched to the output of pulse detection circuits 45 and 45A. Additionally, a maximum-likelihood detector may be included to further correlate the expected time locations of pulses as determined by the linearly-swept wavelength for a fixed cavity length, especially in applications where the time location set for a plurality of pulses is a non-contiguous functions, such as in optical detection systems using a reflector to form a resonator with the encoded surface, where detection subsystem 13 is attempting to discern and differentiate between two or more discrete cavity lengths.

A pulse shape determination block 46A is also coupled to an output of detection subsystem 13 and may measure the width, height or other shape characteristic of pulses received by detection subsystem 13. Width detection may be achieved using a threshold detection that measures the crossing points of a pulse through a particular threshold. Pulse symmetry may be detected by differentiating between the positive and negative transitions and comparing with the output of pulse shape determination block 46A. Pulse height may be measured by one or more thresholds, including analog-to-digital (A/D) conversion systems providing a quasi-continuous measurement range of pulse height.

Also, particular shapes may be correlated or a correlation to one or more predetermined shapes may be compared in order to determine the presence or absence of features on a surface under measurement or other measurement or optical data input to the system. A cavity parameters determination block 48A is coupled to the output of pulse shape determination block 46A for determining cavity parameters as a function of the pulse shape, such as reflectivity/absorption/scattering of a surface under measurement taken as a function of pulse width determined by pulse shape determination block.

Time differencing block 47 determines the differences between the multiple resonant peaks for each detection subsystem 13 and 13A so that a cavity length determination block 48 can extract a cavity length or changes in cavity length of resonator 15, 15A or 15B and a relative cavity length of reference resonator 19. The apparent cavity length of reference resonator 19, is modified by deviations in wavelength of illumination subsystem 11 from the expected wavelength. By comparing the measured cavity length to the known cavity length of reference resonator 19, the wavelength deviation can be established and used to correct the response of detection subsystem 13, improving the resolution and accuracy of the measurement.

The corrected measurement resonator cavity length information or change information may be used directly as a measurement output, for example when one of the resonator surfaces is a surface under measurement and variations in the height of the surface under measurement is the desired measurement or data detection output. A counter 49 is used to count the number of resonance points scanned through by the swept illumination wavelength and can be used to reset ramp generator 52 within sweep control circuit 16. Counter 49 thus ensures that a constant number of resonance points is scanned.

As an alternative to direct measurement output from analysis subsystem 14 while illumination subsystem 11 is in swept-wavelength mode, a sample/hold or programmable tuning source 54 may be used to provide a constant-wavelength mode for illumination source 11. A switch S1 provides selection of constant-wavelength mode vs. swept-wavelength mode and sample/hold may be used to sample a particular point in the ramp generator 52 sweep output corresponding to a particular resonance operating point of reference resonator 19 (not necessarily a resonance peak) or the wavelength of illumination subsystem 11 may be programmed via a programmable register, divider, divider/multiplier loop or other means. Such a configuration provides open-loop control of the operating wavelength of tunable illumination source 11 while in constant-wavelength mode, but representing a highly accurate wavelength as determined by the response of reference resonator 19.

Referring now to FIG. 4, detector 44 and 44A output signals (50, 51) as produced by embodiments of the present invention are depicted over time as the illumination wavelength is swept for the two resonators 15 (or 15A or 15B) and 19. Sweep 50 shows that the measurement resonator path length is shorter than the reference resonator path length, as the peaks are farther apart. Without reference resonator 19 detector 44A response 51, any uncertainty in illumination wavelength would reduce the accuracy of an optical path length determination based on waveform 50. But, by correcting the position of the peaks of waveform 50, by compressing or expanding the time-scale of the figure so that waveform 51 corresponds to the known optical length of reference resonator 19, the resulting measurement of the optical length of resonator 15 (or 15A or 15B) can be determined.

The figure shows a detector 44 and 44A output when the detector is positioned on a light-band fringe position. It is apparent from the figure, that the position of the intensity peaks (which may be translated to intensity nulls for dark-band detector positions) in time, varies with the cavity length as described above. Peak location determination block 46 determines the exact position of the peaks (or nulls for a dark-band detector position) and the spread of the peaks in time is used to determine the cavity length according to the analysis below.

The above-incorporated parent application shows an approximate mathematical relationship between the location of the peaks of the waveforms of FIG. 4 and the optical length of the resonators. By determining a ratio between the measured cavity length of reference resonator 19 as presented by waveform 51, and compressing or expanding the scale of waveform 50 by a corresponding amount, the optical length of resonator 15 (or 15A or 15B) can be determined. Alternatively, more precise calculations can be applied to determine sweep linearity deviations based on the known optical length of reference resonator 19, taking into account variations of higher order than linear variation of optical path length with time.

While the invention has been particularly shown and described with reference to the preferred embodiments thereof, it will be understood by those skilled in the art that the foregoing and other changes in form, and details may be made therein without departing from the spirit and scope of the invention.

What is claimed is:

1. An optical system comprising:
   an optical illumination subsystem for producing an optical beam having a swept wavelength;
   an optical coupler for receiving an output of said optical illumination system;
   a measurement resonator coupled to a first output of said optical coupler for generating a first resonance within a path of said measurement beam;

at least one reference resonator coupled to a second output of said optical coupler for generating at least a second resonance within a path of said reference beam;

a measurement optical detector coupled to said measurement resonator for measuring a measurement intensity of light at said measurement resonator;

at least one reference optical detector coupled to said reference resonator for measuring a reference intensity of light at an associated one of said at least one reference resonator; and a processing subsystem coupled to an output of said measurement optical detector and an output of said at least one reference optical detector for interpreting variations in said measured intensity in conformity with variations in said reference intensity.

2. The optical system of claim 1, wherein said processing subsystem comprises a time domain analysis subsystem coupled to said measurement optical detector and said at least one reference optical detector for extracting a time relation of particular points of intensity variations produced at said measurement resonator and said at least one reference resonator when said wavelength of said optical illumination subsystem is swept.

3. The optical system of claim 1, wherein said processing subsystem corrects said measurement intensity in conformity with said reference intensity, whereby deviations of said measured intensity due to deviations of said wavelength of said optical illumination subsystem from expected values of said wavelength are corrected.

4. The optical system of claim 1, wherein said processing subsystem corrects said measurement intensity in conformity with said reference intensity, whereby deviations of an optical path length of said measurement resonator from an expected value of said optical path length are corrected.

5. The optical system of claim 1, wherein said measurement resonator comprises a Fabry-Perot resonator.

6. The optical system of claim 1, wherein said Fabry-Perot resonator comprises:

a surface of under measurement by said optical system;

a partially reflective surface positioned between said surface under measurement and said measurement optical detector at a tuned optical distance, whereby at a predetermined wavelength of said illumination subsystem, a resonance of said measurement resonator is produced by multiple reflections generated between said surface of measurement and said partially reflective surface.

7. The optical system of claim 6, wherein said partially reflective surface is a substantially planar surface.

8. The optical system of claim 6, wherein said partially reflective surface is a curved surface.

9. The optical system of claim 6, wherein said measurement resonator further includes a lens disposed within said resonator, whereby a region of said surface under measurement is resonantly mapped to a region of said partially reflective surface.

10. The optical system of claim 9, wherein said partially reflective surface is a partially reflective surface deposited on a surface of said lens.

11. The optical system of claim 1, wherein said processing subsystem determines a value of said wavelength of said optical illumination subsystem from a time relation of local extrema of said reference intensity and a predetermined optical path length of said at least one reference resonator, and further determines an optical path length of said measurement resonator in conformity with said determined value of said wavelength.

12. The optical system of claim 1, wherein said measurement resonator has a tunable resonant length responsive to an electrical control signal, wherein said processing system further comprises a control circuit coupled to said measurement resonator for providing said electrical control signal, and wherein said processing system generates said electrical control signal in conformity with said reference intensity, whereby said measurement resonator resonant length is compensated for variations in said wavelength of said optical illumination subsystem.

13. The optical system of claim 1, wherein said at least one reference resonator comprises at least two reference resonators, said at least one reference optical detector comprises at least two optical detectors, each associated and coupled to a particular one of said at least two reference resonators.

14. A method for performing an optical measurement comprising:

generating a swept-wavelength illumination beam;

splitting said illumination into a measurement beam and at least one reference beam;

introducing said at least one reference beam to at least one reference resonator;

introducing said measurement beam to a measurement resonator;

detecting a measurement intensity of light at said measurement resonator;

detecting a reference intensity of light at said at least one reference resonator; and interpreting said measurement intensity in conformity with said reference intensity.

15. The method of claim 14, further comprising:

first determining a time relationship of particular points of said measurement intensity; and second determining a time relationship of other particular points of said reference intensity, and wherein said interpreting is performed in conformity with a result of said first and second determining.

16. The method of claim 14, wherein said evaluating corrects said measurement intensity in conformity with said reference intensity, whereby deviations of said measurement intensity due to deviations of said wavelength of said illumination beam from expected values of said wavelength are corrected.

17. The method of claim 14, wherein said evaluating corrects said measurement intensity in conformity with said reference intensity, whereby deviations of an optical path length of said measurement resonator from an expected value of said optical path length are corrected.

18. The method of claim 14, further comprising forming said measurement resonator by positioning a partially reflective surface at a predetermined optical distance from a surface under measurement, whereby said measurement resonator forms a Fabry-Perot resonator.

19. The method of claim 18, further comprising providing a lens between said partially reflective surface and said surface under measurement, whereby a region of said surface under measurement is resonantly mapped to a region of said partially reflective surface.

20. The method of claim 14, wherein said evaluating subsystem determines a value of said wavelength of said optical illumination subsystem from a time relation of local extrema of said reference intensity and a predetermined optical path length of said reference resonator, and further determines an optical path length of said measurement resonator in conformity with said determined value of said wavelength.

21. The method of claim 14, further comprising tuning a resonant length of said measurement resonator in conformity with said reference intensity, whereby said measurement resonator resonant length is compensated for variations in said wavelength of said optical illumination subsystem.

22. The method of claim 13, wherein said splitting comprises splitting said illumination into a measurement beam and at least two reference beams, and wherein said method further comprises:

introducing a first one of said at least two reference beams to a first reference resonator;

introducing a second one of said at least two reference beams to a second reference resonator;

detecting a first reference intensity of light at said first reference resonator;

detecting a second reference intensity of light at said second reference resonator; and interpreting said measurement intensity in conformity with said first reference intensity and said second reference intensity.

* * * * *